US00PP36435P2

(12) United States Plant Patent
Koot

(10) Patent No.: US PP36,435 P2
(45) Date of Patent: Feb. 11, 2025

(54) ***LANTANA* PLANT NAMED 'Dolantralapi'**

(50) Latin Name: *Lantana camara*
Varietal Denomination: Dolantralapi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/662,982

(22) Filed: May 13, 2024

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 6/86; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lantana* plant named 'Dolantralapi', characterized by its initially upright to outwardly spreading and trailing plant habit; vigorous growth habit and rapid growth rate; freely branching growth habit; dense and bushy plant form; dark green-colored leaves; early and freely flowering habit; long flowering period; flowers that are purple to light purple in color with white-colored centers; and good garden performance.

2 Drawing Sheets

Figure 1:
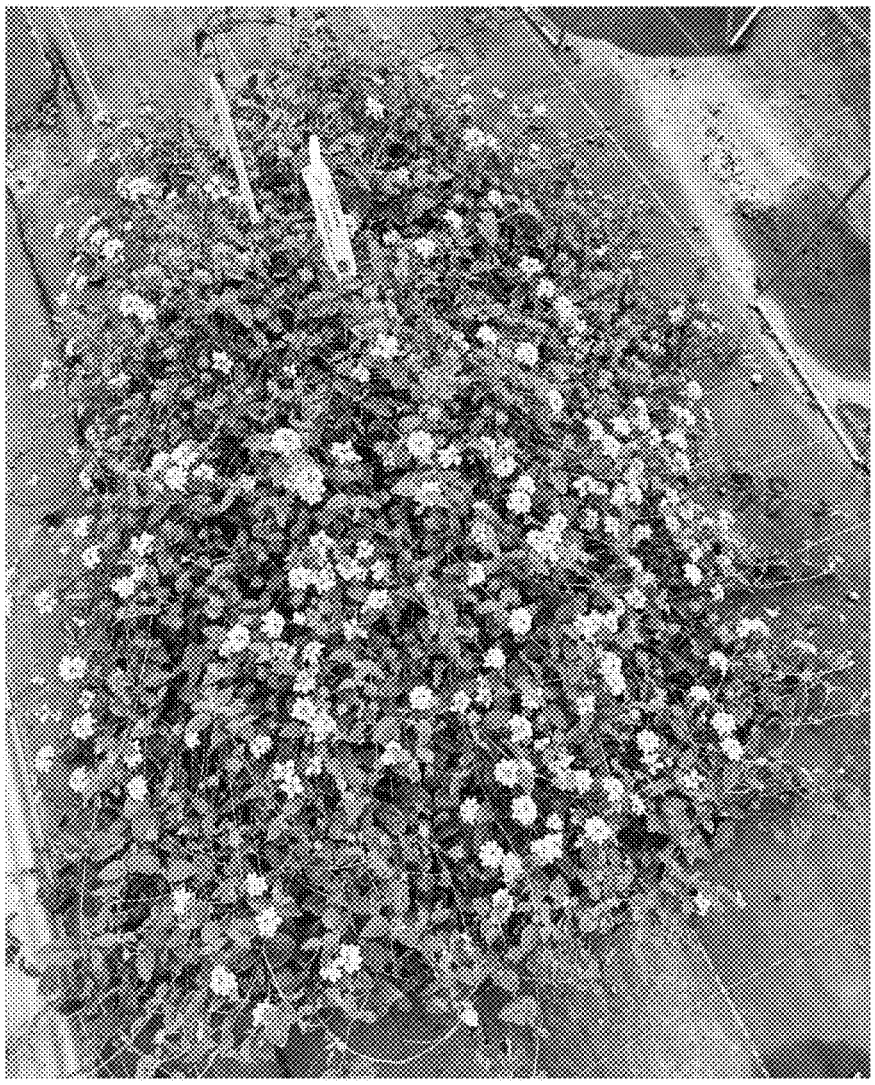

Botanical designation: *Lantana camara.*
Cultivar denomination: 'DOLANTRALAPI'.

STATEMENT REGARDING PRIOR DISCLOSURES BY INVENTOR AND APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Lantana* plant, botanically known as *Lantana camara* and hereinafter referred to by the name 'Dolantralapi'.

The new *Lantana* plant is a product of a planned breeding program conducted by the Inventor in Rheinberg, Germany. The objective of the breeding program is to create new compact, freely-branching *Lantana* plants with early and freely flowering habit and large attractive flowers.

The new *Lantana* plant is a naturally-occurring whole plant mutation of *Lantana camara* 'Trailing Lavender', not patented. The new *Lantana* plant was discovered and selected by the Inventor as a single flowering plant from within a population of plants of 'Trailing Lavender' in a controlled greenhouse environment in Rheinberg, Germany in June 2022.

Asexual reproduction of the new *Lantana* plant by terminal vegetative cuttings in a controlled greenhouse environment in Rheinberg, Germany since July 2022 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dolantralapi'. These characteristics in combination distinguish 'Dolantralapi' as a new and distinct *Lantana* plant:

1. Initially upright to outwardly spreading and trailing plant habit.
2. Vigorous growth habit and rapid growth rate.
3. Freely branching growth habit; dense and bushy plant form.
4. Dark green-colored leaves.
5. Early and freely flowering habit.
6. Long flowering period.
7. Flowers that are purple to light purple in color with white-colored centers.
8. Good garden performance.

Plants of the new *Lantana* can be compared to plants of the mutation parent, 'Trailing Lavender'. Plants of the new *Lantana* differ primarily from plants of 'Trailing Lavender' in the following characteristics:

1. Plants of the new *Lantana* are more uniform than and not as open as 'Trailing Lavender'.
2. Plants of the new *Lantana* are more freely branching than of 'Trailing Lavender'.
3. Plants of the new *Lantana* are more freely flowering than of 'Trailing Lavender'.

4. Flowers of plants of the new *Lantana* are lighter purple in color than flowers of plants of 'Trailing Lavender'.

Plants of the new *Lantana* can be compared to plants of the *Lantana montevidensis* 'Robpwpur', disclosed in U.S. Plant Pat. No. 19,357. In side-by-side comparisons, plants of the new *Lantana* differ from plants of 'Robpwpur' in the following characteristics:

1. Plants of the new *Lantana* are more uniform than and not as open as 'Robpwpur'.
2. Plants of the new *Lantana* are more freely branching than of 'Robpwpur'.
3. Flowers of plants of the new *Lantana* are darker purple in color than flowers of plants of 'Robpwpur'.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph on the first sheet (FIG. 1) is a top perspective view of a typical flowering plant of 'Dolantralapi' grown in a container.

Figure 2:
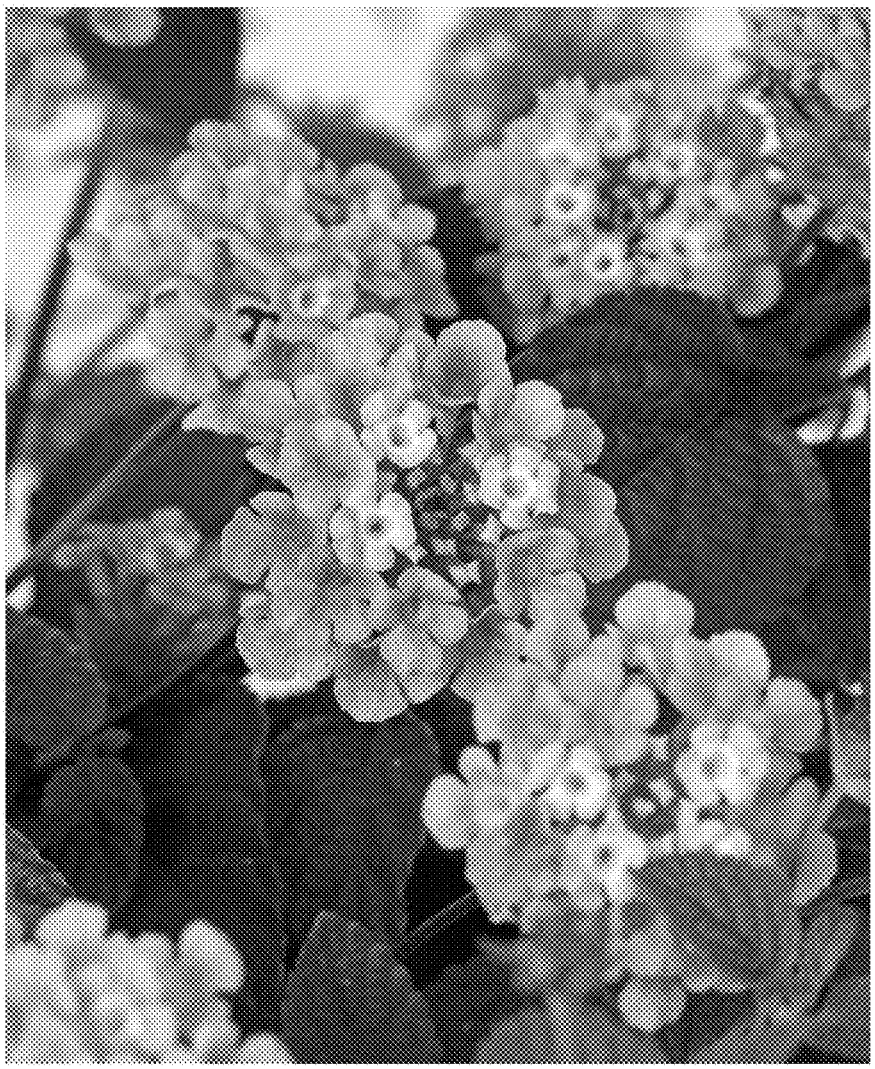

The photograph on the second sheet (FIG. 2) is a close-up view of a typical flowering plant of 'Dolantralapi'.

DETAILED BOTANICAL DESCRIPTION

The aforementioned photographs and following observations and measurements describe plants grown during the spring and summer in 15-cm containers in a glass-covered greenhouse in Rheinberg, Germany and under commercial practices typical of commercial *Lantana* production. During the production of the plants, day and night temperatures averaged 18° C. and light levels averaged 4,500 lux. Plants were pinched three weeks after planting and were twelve weeks old when the photographs were taken and 15 weeks old when the description was taken. In the following description, color references are made to The Royal Horticultural Society Colour Chart, Fifth Edition, except where general terms of ordinary dictionary significance are used.

Botanical classification: *Lantana camara* 'Dolantralapi'.

Parentage: Naturally-occurring whole plant mutation of *Lantana camara* 'Trailing Lavender', not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically whit in color, actual color of the roots is dependent on substrate composition, water quality, fertilizers, substrate temperature and age of roots.

*Rooting habit*.—Freely branching; dense.

Plant description:

*Plant and growth habit*.—Initially upright to outwardly spreading and trailing plant habit; vigorous growth habit and rapid growth rate; freely branching habit, dense and bushy plant form.

*Plant height, soil level to top of foliar plane*.—About 13 cm.

*Plant height, soil level to top of floral plane*.—About 14 cm.

*Plant diameter*.—About 62.5 cm.

Lateral branch description:

*Branching habit*.—Freely branching habit with about six primary lateral branches each with at least eleven secondary lateral branches developing per plant.

*Length*.—About 80 cm.

*Diameter*.—About 4 mm.

*Internode length*.—About 5.5 cm.

*Strength*.—Moderately strong.

*Texture and luster*.—Pubescent; matte; longitudinally ridged.

*Color, developing stems*.—Close to 143C variably tinged with N77A.

*Color, developed stems*.—Close to 144A.

Leaf description:

*Arrangement*.—Opposite, simple.

*Length*.—About 4.1 cm.

*Width*.—About 2.4 cm.

*Shape*.—Ovate.

*Apex*.—Acute.

*Base*.—Obtuse.

*Margin*.—Serrate.

*Texture and luster, upper and lower surfaces*.—Slightly pubescence; matte.

*Venation pattern*.—Pinnate, reticulate.

*Color*.—Developing leaves, upper surface: Close to 137A. Developing leaves, lower surface: Close to 138B. Fully expanded leaves, upper surface: Close to N137D; venation, close to 137B. Fully expanded leaves, lower surface: Close to 139C; venation, close to 139C to 139D.

*Petioles*.—Length: About 6 mm. Diameter: About 1 mm. Strength: Moderately strong. Texture and luster: Smooth, glabrous; matte. Color, upper surface: Close to 139C. Color, lower surface: Close to 138B.

Flower description:

*Flower arrangement and flowering habit*.—Solitary salverform flowers arranged in terminal and axillary hemispherical umbels; flowers face mostly upward or outward depending on the position in the umbel; freely flowering habit with about 14 open flowers per inflorescence with numerous inflorescences developing per plant and more than 400 flowers developing per plant during the flowering season; flowers sessile.

*Natural flowering season*.—Early flowering habit, depending on temperature, plants begin flowering about five to ten weeks from unrooted cuttings; long flowering period, plants of the new *Lantana* flower continuously from the spring throughout the summer in Germany.

*Flower longevity on the plant*.—Depending on temperatures, individual flowers last about five to six days; flowers not persistent.

*Fragrance*.—Moderate, pleasant.

*Inflorescence height*.—About 1.65 cm.

*Inflorescence diameter*.—About 2.5 cm.

*Flower buds*.—Length: About 5.5 mm. Diameter: About 1.3 mm. Shape: Tubular. Texture and luster: Smooth, glabrous; matte. Color: Close to 4C and 76A.

*Flowers*.—Appearance: Flared trumpet, salverform; corolla fused, four-parted. Diameter: About 8 mm by 9 mm. Depth (height): About 1.3 cm. Throat diameter: About 1 mm. Tube length: About 8.5 mm. Tube diameter: About 1 mm.

*Corolla*.—Arrangement: Single whorl of four fused petals; two petals larger than the other two petals. Larger petals lobe length: About 4 mm. Larger petals lobe width: About 4 mm. Smaller petals lobe length: About 3 mm. Smaller petals lobe width: About 3 mm. Petal lobe shape: Obovate. Petal lobe apex: Rounded. Petal margin: Entire; very slightly undulate. Petal texture and luster, upper and lower surfaces: Smooth, glabrous; matte. Throat texture and luster: Smooth, glabrous; matte. Tube texture and luster: Smooth, glabrous; matte. Color: When opening, upper surface: Close to 77B. When opening, lower surface: Close to 77C. Fully opened, upper surface: Close to 77B and 77C; venation, close to 77B to 77C; color becoming closer to 77B with subsequent development. Fully opened, lower surface: Close to 76A, 76B and 77B; venation, close to 76A to 76B; color becoming closer to 77D with subsequent development. Throat: Distally, close to NN155C; proximally, close to 7A; venation, similar to lamina colors. Tube: Distally, close to N78D and proximally, close to 155C; venation, similar to lamina colors.

*Calyx*.—Appearance: Tubular calyx with four to five fused sepals. Sepal length: About 8.5 mm. Sepal diameter: About 5 mm. Sepal shape: Lanceolate. Sepal apex: Apiculate. Sepal margin: Entire. Sepal texture and luster, upper and lower surfaces: Coarse pubescence; matte. Sepal color, upper surface: Close to N137D, 138A, 139D and/or 145C. Sepal color, lower surface: Close to 138A, 139D and/or 145C.

*Reproductive organs*.—Stamens: Quantity and arrangement: Four per flower, adnate to floral tube. Filament length: About 0.9 mm. Filament color: Close to 155B. Anther length: About 0.5 mm. Anther shape: Ellipsoidal. Anther color: Close to 199A and 199B. Pollen amount: None observed. Pistils: Quantity: One per flower. Pistil length: About 2 mm. Style length: About 1.3 mm. Style color: Close to 157B. Stigma diameter: About 0.3 mm. Stigma shape: Round. Stigma color: Close to 137A. Ovary color: Close to 138A and 138B. Fruits/seeds: To date, fruit and seed development have not been observed on plants of the new *Lantana*.

Garden performance: Plants of the new *Lantana* have been observed to have good garden performance and to tolerate wind, rain and to tolerate temperatures from about 5° C. to about 40° C.

Pathogen & pest tolerance: To date, plants of the new *Lantana* have not been observed to be tolerant to pathogens and pests common to *Lantana* plants.

It is claimed:

1. A new and distinct *Lantana* plant named 'Dolantralapi' as illustrated and described herein.

* * * * *